United States Patent [19]

Fruehwirth

[11] Patent Number: Plant 7,711

[45] Date of Patent: Nov. 12, 1991

[54] POINSETTIA PLANT '15-88'

[75] Inventor: Franz Fruehwirth, Encinitas, Calif.

[73] Assignee: Paul Ecke Ranch, Inc., Encinitas, Calif.

[21] Appl. No.: 528,235

[22] Filed: May 24, 1990

[51] Int. Cl.[5] ..... A01H 5/00

[52] U.S. Cl. ..... Plt./86

[58] Field of Search ..... Plt./86, 86.1, 86.3

*Primary Examiner*—Howard J. Locker

*Attorney, Agent, or Firm*—Arnold, White & Durkee

[57] ABSTRACT

Poinsettia '15-88' is a cultivar having unusual bicolored pink bracts. It is a sport of 'V-14 Hot Pink' (U.S. Plant Pat. No. 5,497) and has the same physical traits and growth characteristics as the parent plant. The new plant has self-branching characteristics and produces a very desirable branched flowering pot plant.

1 Drawing Sheet

BACKGROUND OF THE NEW PLANT

This new Poinsettia cultivar originated in 1985 as a sport of 'V-14 Hot Pink' (U.S. Plant Pat. No. 5,497) in my greenhouse in Encinitas, Calif. It was selected because of its unusual bicolored pink flower bracts, traits which distinguish it from other poinsettia cultivars and seem to make it a desirable plant for commercial greenhouse production. It has all of the desirable vigor, self-branching and large flower bract characteristics as the other color sports of the 'V-14' (U.S. Plant Pat. No. 4,384) family of Poinsettias. The pink color of the bracts is soft and the bicolor contrast is somewhat muted. After selection, stem cuttings of this plant were vegetatively produced for test purposes in Encinitas, Calif., and clones of this plant were subjected to successive generations of vegetative propagation. The physical traits and growth characteristics remain stable from generation to generation.

DESCRIPTION OF THE PHOTOGRAPHS

Poinsettia '15-88' is illustrated in the accompanying color photographs. The upper photo is a side view of typical unpinched plants in full flower. The lower photo is a top view of plants showing flower and bract formation.

DESCRIPTION OF THE PLANT

The following is a detailed description of this new poinsettia as observed in my greenhouse in Encinitas, Calif., during December 1989. Observations were recorded from flowering plants, grown as 3 unpinched plants per pot. The pot was 14 cm. in diameter and 11 cm. in height. Color designations are compared to the 1986 edition of R.H.S. Colour Chart, first published in 1966 by The Royal Horticultural Society, London, England.

The Plant

Origin: Sport of 'V-14 Hot Pink' (U.S. Plant Pat. No. 5,497)

Classification:

*Botanic.*—*Euphorbia pulcherrima* Willd.

*Common name.*—Poinsettia.

*Cultivar name.*—'15-88'.

Form: Shrub.

Height: Medium.

Growth habit: As a single stemmed plant, upright and vigorous. In full flower, the stem is terminated by a large inflorescence, with several smaller flowering side shoots lower on the stem. I observed 3 plants in a pot with an overall height of 38 cm. and an overall width of 54 cm. The bract diameter of individual flowers was 32 cm.

Branching: Branching can be enhanced by removal of the stem tip. Then, several flowering branches with equal vigor may develop on a single plant.

Growth rate: Very fast. Rooting of stem cuttings occurs in 12–18 days under intermittent mist. The plant will flower in about ten weeks under continuous long night conditions and night temperatures of about 16–18 degrees C.

Foliage: The foliage is clean and uniformly green from bottom to top of the plant. The leaves are of medium size, leaf blades typically being about 13–14 cm. long and about 9–10 cm. wide with leaf petioles about 6–8 cm. long.

*Leaf shape.*—Typical leaves are ovate with obtuse bases and acuminate tips. Leaf margins are mostly lobed, with 1–2 lobes and numerous small marginal indentations on each side of the leaf blade.

*Color.*—Upper side — Green, darker than RHS 137A. Under side — Green, near RHS. 137B.

*Retention.*—The foliage retention is good even under low light intensities in the consumer's home.

Bracts: Generally there are 15–21 bicolored pink bracts of various sizes subtending the cyathia. The primary bracts have blades typically 17–18 cm. long and 10–12 cm. wide with petioles about 3 cm. long.

*Shape.*—Bracts are mostly ovate to elliptic with acute bases and acuminate tips. Primary bracts are mostly entire with some slight lobing.

*Color.*—Upper side — Bicolored: Pink, with 2 shades of pink on each bract. An irregular area of the darker pink, near R.H.S. 54B, is located at the center of the bract, usually on either side of the mid-vein. The lighter pink, near RHS 38C, is located peripherally. Under side — Bicolored: Pink, with 2 shades of pink. The patterns of each color mirror the upper surface. The darker inner color is near RHS 51C and the lighter peripheral color near RHS 49D.

Flowers: Generally, 12–15 cyathia (flowers) are present when the plant is in full bloom. Each cyathium is about 7–8 mm long and about 5 mm wide, green in color with a yellow fringe at the distal end. One yellow nectar cup protrudes from the side of each cyathium. The flower pedicel is also green and about 5–6 mm long. The stamens protruding from the cyathia are pinkish white.

What is claimed is:

1. A new and distinct Poinsettia cultivar, substantially as herein shown and described, characterized by its bicolored pink flower bracts.

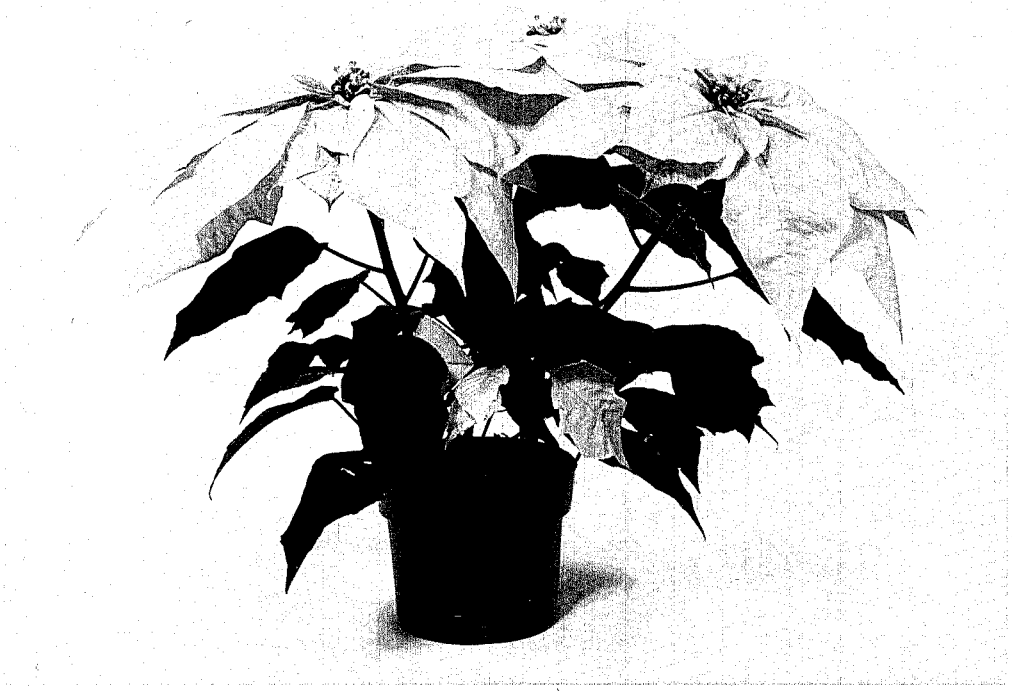
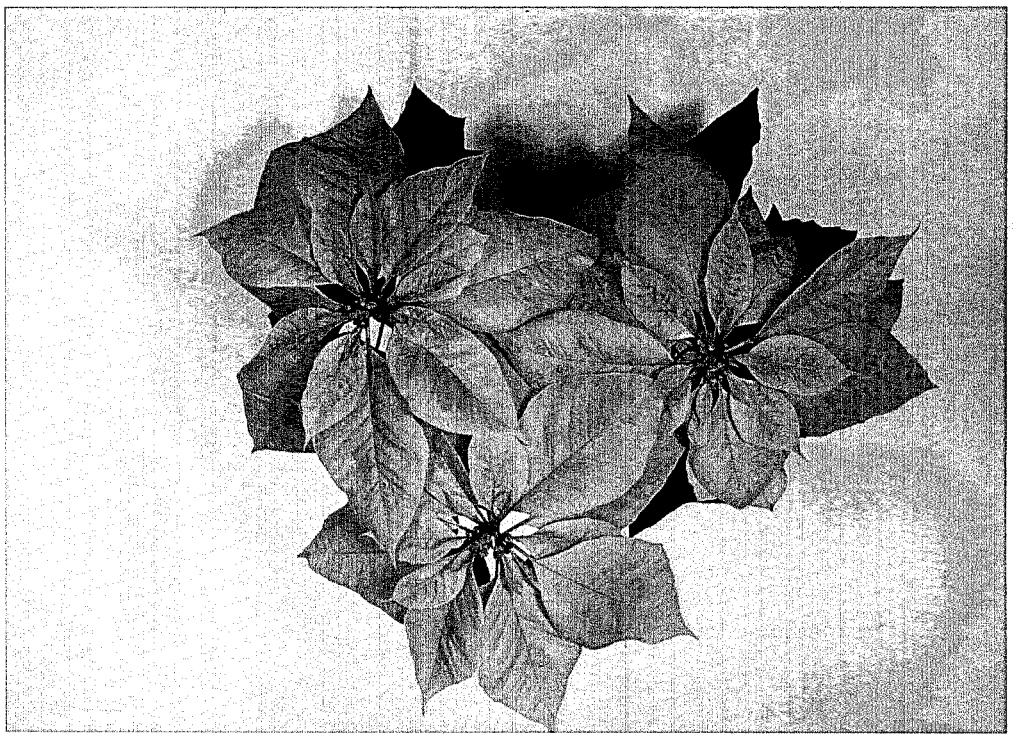

* * * * *